US010314993B2

United States Patent
Hansen et al.

(10) Patent No.: US 10,314,993 B2
(45) Date of Patent: Jun. 11, 2019

(54) LARYNGEAL MASK

(71) Applicant: AMBU A/S, Ballerup (DK)

(72) Inventors: Jan Guldberg Hansen, Greve (DK); Troels Nicolaj Qvist, Roskilde (DK); Peer Hoffmann, Stenløse (DK); Erik Øllgaard Helmsen, Espergærde (DK); Lasse Kjeld Gjøske Petersen, Frederiksværk (DK)

(73) Assignee: AMBU A/S, Ballerup (DK)

( * ) Notice: Subject to any disclaimer, the term of this patent is extended or adjusted under 35 U.S.C. 154(b) by 678 days.

(21) Appl. No.: 14/898,424

(22) PCT Filed: Jun. 20, 2013

(86) PCT No.: PCT/DK2013/050201
§ 371 (c)(1),
(2) Date: Dec. 14, 2015

(87) PCT Pub. No.: WO2014/202078
PCT Pub. Date: Dec. 24, 2014

(65) Prior Publication Data
US 2016/0136373 A1 May 19, 2016

(51) Int. Cl.
*A61M 16/04* (2006.01)
*B29D 23/00* (2006.01)

(52) U.S. Cl.
CPC .... *A61M 16/0445* (2014.02); *A61M 16/0409* (2014.02); *A61M 16/0415* (2014.02);
(Continued)

(58) Field of Classification Search
CPC .............. A61M 16/04; A61M 16/0409; A61M 16/0415; A61M 16/0431; A61M 16/0445;
(Continued)

(56) References Cited

U.S. PATENT DOCUMENTS

| 4,509,514 A | 4/1985 | Brain |
| 4,995,338 A | 2/1991 | Morita et al. |

(Continued)

FOREIGN PATENT DOCUMENTS

| CN | 2882657 | 3/2007 |
| CN | 101057994 | 10/2007 |

(Continued)

OTHER PUBLICATIONS

Office Action (Chinese language), issued by the Chinese Patent Office, dated Sep. 2, 2016, for corresponding Chinese patent application No. 201380077481X, 8 pages.
(Continued)

*Primary Examiner* — Joseph D. Boecker
(74) *Attorney, Agent, or Firm* — Faegre Baker Daniels LLP

(57) ABSTRACT

A laryngeal mask (1) comprising an air-way tube (2) and a mask portion (6) with an inflatable cuff (8) which is arranged around the airway tube (2) at the distal end thereof. A gastric tube (12) which extends at least partially along the outer surface of the airway tube (2), penetrates through the wall of said inflatable cuff (8) at a first location, extends through said inflatable cuff (8), and ends in a connection to an opening (12) in the wall of the cuff at a second location at the tip part of the laryngeal mask, so as to provide a passage through said circumferential cuff. With respect to a central mirror symmetry plane said gastric tube extends along the outer surface of the airway tube (2) in an asymmetrical manner, through said inflatable cuff (8) at the first location arranged asymmetrically with respect to said central plane, through said inflatable cuff (8), and ends in the connection to the wall of the cuff (8) at the second location at the tip part.

19 Claims, 5 Drawing Sheets

Figure 1:
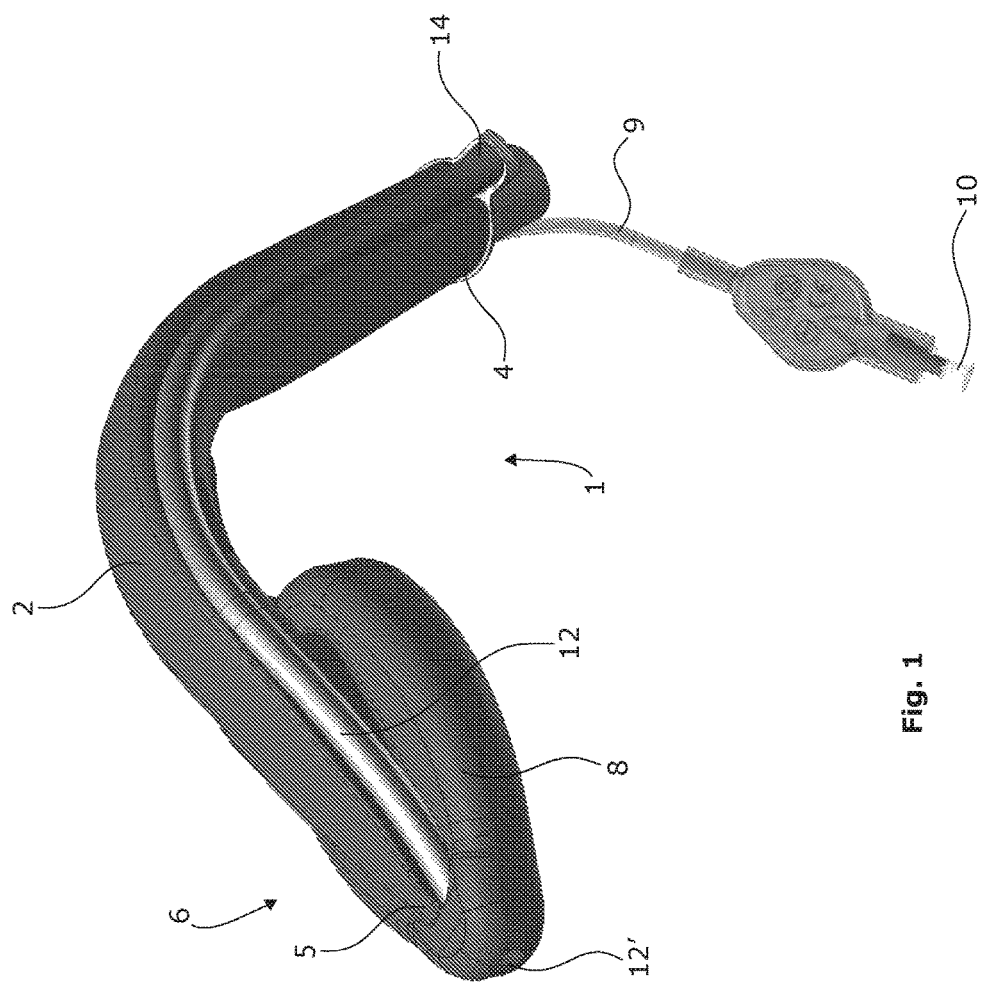

(52) U.S. Cl.
CPC .... *A61M 16/0447* (2014.02); *A61M 16/0463* (2013.01); *A61M 16/0497* (2013.01); *B29D 23/00* (2013.01); *A61M 2207/10* (2013.01)

(58) Field of Classification Search
CPC .......... A61M 16/0447; A61M 16/0463; A61M 16/0497; A61M 2207/00; A61M 2207/10; B29D 23/00
See application file for complete search history.

(56) References Cited

U.S. PATENT DOCUMENTS

| | | | |
|---|---|---|---|
| 5,241,956 A | 9/1993 | Brain | |
| 5,391,248 A | 2/1995 | Brain | |
| 5,632,271 A | 5/1997 | Brain | |
| 2003/0037790 A1* | 2/2003 | Brain | A61M 16/04 128/207.14 |
| 2003/0051734 A1* | 3/2003 | Brain | A61M 16/04 128/207.15 |
| 2004/0020491 A1* | 2/2004 | Fortuna | A61M 16/04 128/207.15 |
| 2004/0089307 A1* | 5/2004 | Brain | A61M 16/04 128/207.14 |
| 2005/0081861 A1* | 4/2005 | Nasir | A61M 16/04 128/207.14 |
| 2006/0207601 A1* | 9/2006 | Nasir | A61M 16/04 128/207.14 |
| 2008/0099026 A1* | 5/2008 | Chang | A61M 16/0463 128/207.15 |
| 2011/0023890 A1* | 2/2011 | Baska | A61M 16/04 128/207.15 |
| 2011/0220117 A1* | 9/2011 | Dubach | A61M 16/04 128/207.14 |
| 2011/0226256 A1 | 9/2011 | Dubach | |
| 2011/0277772 A1* | 11/2011 | Nasir | A61D 7/04 128/207.15 |
| 2012/0211010 A1 | 8/2012 | Brain | |
| 2013/0239959 A1* | 9/2013 | Brain | A61M 16/04 128/202.16 |
| 2013/0269689 A1* | 10/2013 | Brain | A61M 16/04 128/200.26 |
| 2015/0114400 A1 | 4/2015 | Dubach | |
| 2015/0128946 A1* | 5/2015 | Stix | A61M 16/0409 128/204.18 |
| 2015/0144134 A1* | 5/2015 | Dubach | A61M 16/04 128/202.27 |
| 2016/0008562 A1* | 1/2016 | Sagales Manas | A61B 1/267 600/109 |

FOREIGN PATENT DOCUMENTS

| | | |
|---|---|---|
| CN | 201832255 | 5/2011 |
| WO | WO/1997/12640 | 4/1997 |
| WO | WO 2001/024860 | 4/2001 |
| WO | WO/2004/089453 | 10/2004 |
| WO | WO/2008/001724 | 3/2008 |
| WO | WO/2012/049448 | 4/2012 |
| WO | WO/2013/079902 | 6/2013 |

OTHER PUBLICATIONS

English translation of Office Action, issued by the Chinese Patent Office, dated Sep. 2, 2016, for corresponding Chinese patent application No. 201380077481X, 7 pages.
International Search Report issued by the European Patent Office in related International Application No. PCT/DK2013/050201, dated Mar. 25, 2014, 3 pages.

* cited by examiner

LARYNGEAL MASK

The present U.S. non-provisional patent application is a National stage entry of International Application No. PCT/DK2013/050201, filed Jun. 20, 2013, titled "A LARYNGEAL MASK". The disclosure of International Application No. PCT/DK2013/050201 is incorporated herein by reference in its entirety. U.S. Pat. No. 9,889,264, issued Feb. 13, 2018, and U.S. Pat. No. 10,149,955, issued Dec. 11, 2018, are continuations-in-part of the present application.

The present invention relates to laryngeal masks, in particular a laryngeal mask with gastric access, and more specifically a laryngeal mask comprising an airway tube having an inner lumen following a predetermined curve in a central mirror symmetry plane about which the inner lumen is generally mirror symmetrical, an outer surface, a proximal end and a distal end, a mask portion being arranged around the airway tube at the distal end thereof, the inner lumen of the airway tube thus communicating with or forming a mask lumen in said mask portion, said mask portion comprising a circumferential cuff comprising an inflatable inner volume delimited by a closed tubular wall, arranged at the periphery of the mask portion and generally surrounding said mask lumen, the circumferential cuff having a shape presenting a tip part at the distal end of the laryngeal mask, a gastric tube which extends at least partially along the outer surface of the airway tube, penetrates through said closed tubular wall at a first location, extends through said inflatable volume and ends in a connection to an opening in the closed tubular wall at a second location at the tip part, so as to provide a passage through said circumferential cuff.

Laryngeal masks are used in connection with the establishment of passage of air to the respiratory tracts, while simultaneously blocking the air passage to the oesophagus. The laryngeal mask is shaped such that it has a lumen within a mask portion arranged at the distal end of an airway tube, i.e. the end of the airway tube facing towards the laryngeal opening, when the laryngeal mask is correctly placed in a patient and the cuff inflated. Around that lumen a generally elliptical, inflatable, peripheral cuff is provided, so as to form a seal around the laryngeal opening when the laryngeal mask is correctly placed in a patient and the cuff inflated. In order to be able to inflate the cuff, an inflation tube is connected to an inflation means, such as a balloon and a valve outside the patient. Operating the inflation means allows the peripheral cuff of the laryngeal mask to be inflated thereby ensuring a tight abutment of the laryngeal mask. Using the valve, the peripheral cuff may be deflated when the laryngeal mask is no longer needed and has to be removed from the patient.

With the proviso for the generally highly flexible inflation tube the laryngeal mask disclosed in U.S. Pat. No. 5,241,956 discloses a generally mirror symmetrical laryngeal mask, where the right-hand side and the left-hand side of a central plane are otherwise identical. In the following description the left-hand side and the right-hand side will be understood as corresponding to the left-hand side and the right-hand side of the patient when the laryngeal mask is correctly inserted into the patient. Similar terms such as front and back are to be understood in corresponding sense, i.e. as they would commonly be used for the patient.

As explained in U.S. Pat. No. 5,241,956 it is advantageous if the laryngeal mask is fitted with a passage for gastric access, e.g. for allowing gastric content to be evacuated or drained even though the passage to the oesophagus is blocked by the inflated cuff. Since the cuff is adapted to block the oesophagus, the passage provided as a gastric tube must pass through the cuff in order for its distal end to provide an opening in the outer surface of the cuff. In U.S. Pat. No. 5,241,956 different embodiments of how to arrange the gastric tube with respect to the airway tube and how to pass it through the cuff are disclosed. As mentioned above the laryngeal mask of U.S. Pat. No. 5,241,956 generally exhibits mirror symmetry, and this applies also to the disclosed arrangements of the gastric tube. In one embodiment the gastric tube extends in the central plane along the back of the airway tube all the way to the back of the inflatable cuff, and passes through the cuff in order to present an opening at the distal end of the laryngeal mask. In another embodiment the gastric tube is bifurcated extending along either side of the airway tube in mirror image symmetry, and joining in the central plane just before the gastric tube passes through the cuff in a manner similar to the first embodiment in order to present an opening at the distal end of the laryngeal mask.

Other prior art laryngeal masks, such as disclosed in U.S. Pat. Nos. 4,995,338, 5,391,248, 4,509,514 and WO-A2004/089453, exhibit similar mirror symmetry, at least as far as the parts inserted into the patient is concerned.

Though this mirror symmetry is largely desired because the parts of the human body where the laryngeal mask is used is generally also mirror symmetrical, it does present some drawbacks in terms of manufacturing the laryngeal mask.

Based on the above it is the object of the present invention to provide a laryngeal mask overcoming the above drawbacks, while still exhibiting a large degree of symmetry.

According to a first aspect of the invention this object is achieved by a laryngeal mask comprising an airway tube having an inner lumen following a predetermined curve in a central mirror symmetry plane about which the inner lumen is generally mirror symmetrical, an outer surface, a proximal end and a distal end, a mask portion being arranged around the airway tube at the distal end thereof, the inner lumen of the airway tube thus communicating with or forming a mask lumen in said mask portion, said mask portion comprising an circumferential cuff comprising an inflatable inner volume delimited by a closed tubular wall, arranged at the periphery of the mask portion and generally surrounding said mask lumen, the circumferential cuff having a shape presenting a tip part at the distal end of the laryngeal mask, a gastric tube which extends at least partially along the outer surface of the airway tube, penetrates through said closed tubular wall at a first location, extends through said inflatable volume, and ends in a connection to an opening the closed tubular wall at a second location at the tip part so as to provide a passage through said circumferential cuff, characterized in that, with respect to said central mirror symmetry plane, said gastric tube extends along the outer surface of the airway tube in an asymmetrical manner, through said closed tubular wall at a first location arranged asymmetrically with respect to said central plane, through said inflatable volume, and ends in a connection to the closed tubular wall at a second location at the tip part so as to provide a passage through said circumferential cuff.

With this arrangement it becomes easier to manufacture the laryngeal mask. The airway tube and the mask portion with the cuff may be moulded in one single piece. Mounting the gastric tube in this single piece is facilitated because the access to the sites where the two parts are to be joined together is improved. Moreover, this asymmetry is advantageous because even though the human body, as mentioned above, exhibits a great deal of symmetry it is not entirely symmetrical, and the entry to the esophagus is slightly off-set towards the left-hand side of the body. Consequently the asymmetry facilitates the insertion of a catheter or the like via the gastric tube into the esophagus because during insertion, the catheter is guided by the gastric tube and will therefore have a tendency to exit pointing to the left corresponding to the asymmetry of the human body at the entry of the esophagus.

According to a first preferred embodiment, said first location is arranged at the back of the tubular cuff, i.e. the part of the cuff facing towards the back of the patient, when the laryngeal mask is correctly inserted in the patient.

This allows easy insertion of the gastric tube into the cuff before it is joined with the cuff, and provides good access to the first and second locations when joining the gastric tube to the cuff by e.g. gluing.

According to another preferred embodiment, said outer surface comprises a recess adapted to accommodate the gastric tube. This allows the preservation of a great deal of overall symmetry while at the same time arranging the gastric tube in a location where it does not press against and irritate the pharynx.

This may be further improved if, according to a further preferred embodiment, the depth of the recess varies along the length of the airway tube.

According to yet a further embodiment, the outer surface of the airway tube presents a protrusion adjacent said recess so as to increase the depth of said recess. This allows the relative deviations from symmetry compared to the dimensions of the laryngeal mask perpendicular to the mirror symmetry plane to be kept small where the dimensions perpendicular to the mirror symmetry plane are small.

According to a preferred embodiment, the depth variation of the recess comprises a salient shelf provided in an area on the outer surface of the airway tube corresponding to an area where the inner lumen of the airway tube transitions into the mask lumen. Using a salient shelf provides additional support of the gastric tube in selected places. With the additional support for the gastric tube from the salient shelf, the gastric tube itself becomes capable of providing support for other parts of the outer wall of the airway tube. This, in turn, means the outer wall of the airway tube may be made much thinner. When the distal end of the airway tube has a taper towards the mask portion, this means that the gastric tube may be located closer to the mirror image symmetry plane, thus allowing the laryngeal mask to present a higher degree of symmetry even where the airway tube has a taper.

According to another embodiment, the short stub is provided at an angle adapted to point towards the side of the plane in which the aperture is offset, preferably towards the aperture and recess leading to the aperture. This allows easy connection of the short stub to the gastric tube. Furthermore, this configuration ensures a better guiding of the cathether towards the entrance of esophagus.

Figure 2:
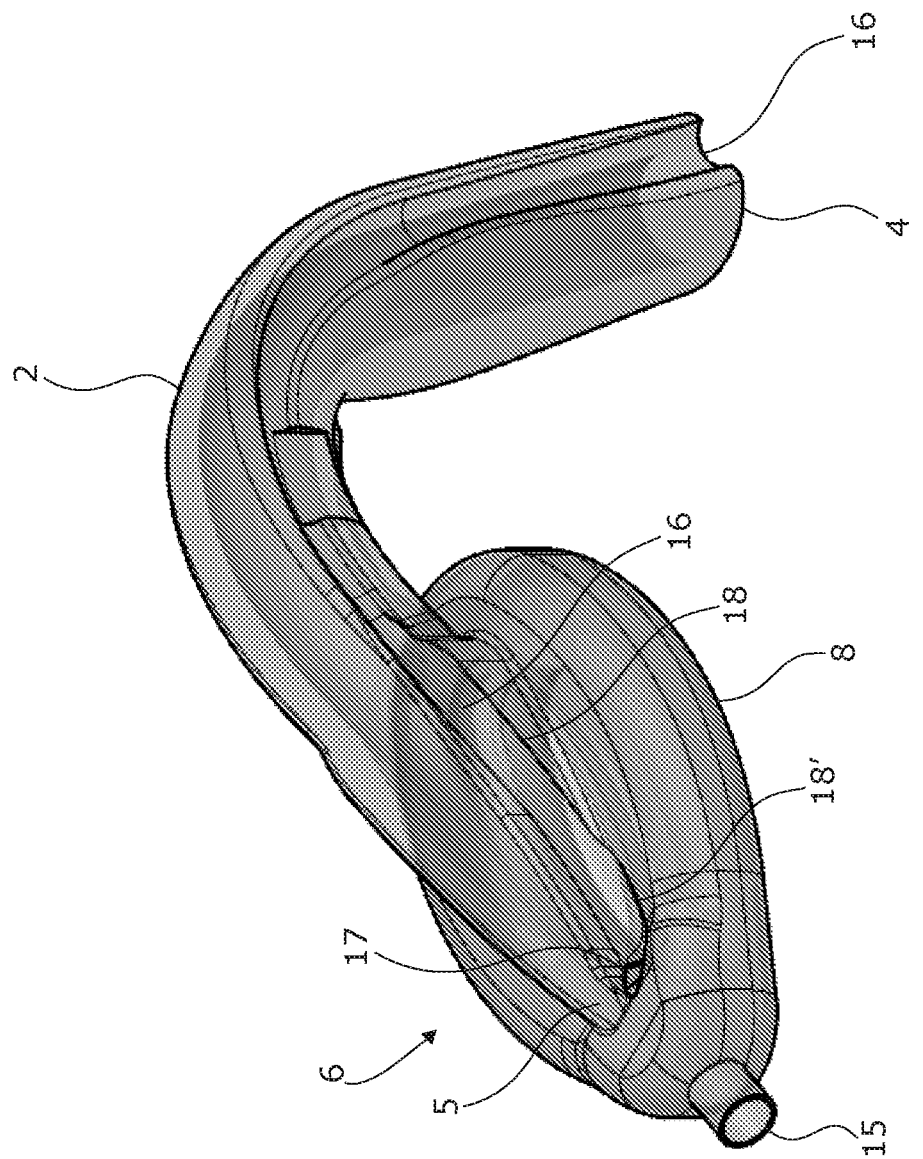
Figure 3:
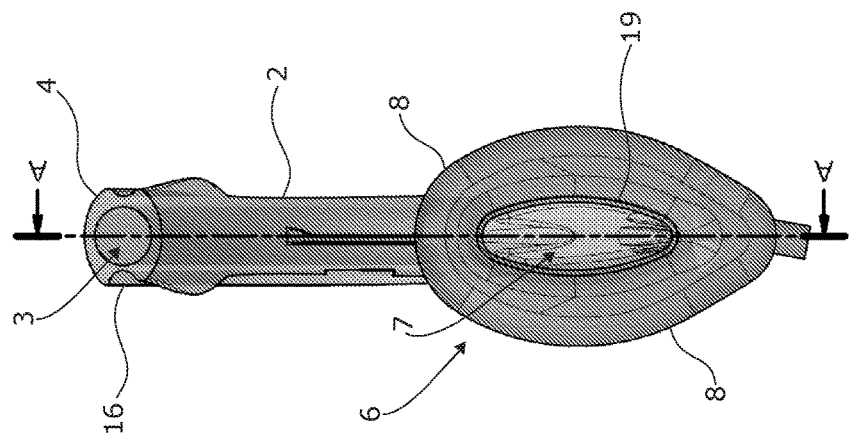
Figure 6:
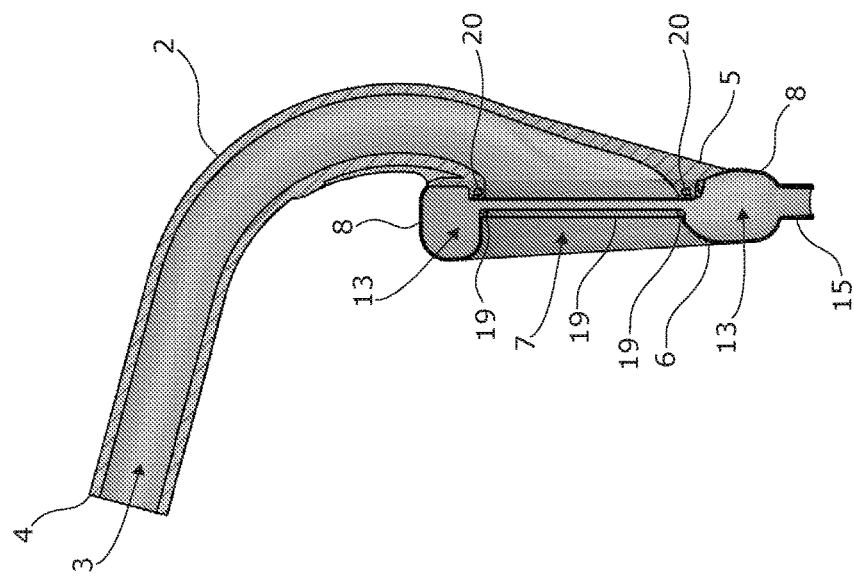
Figure 4:
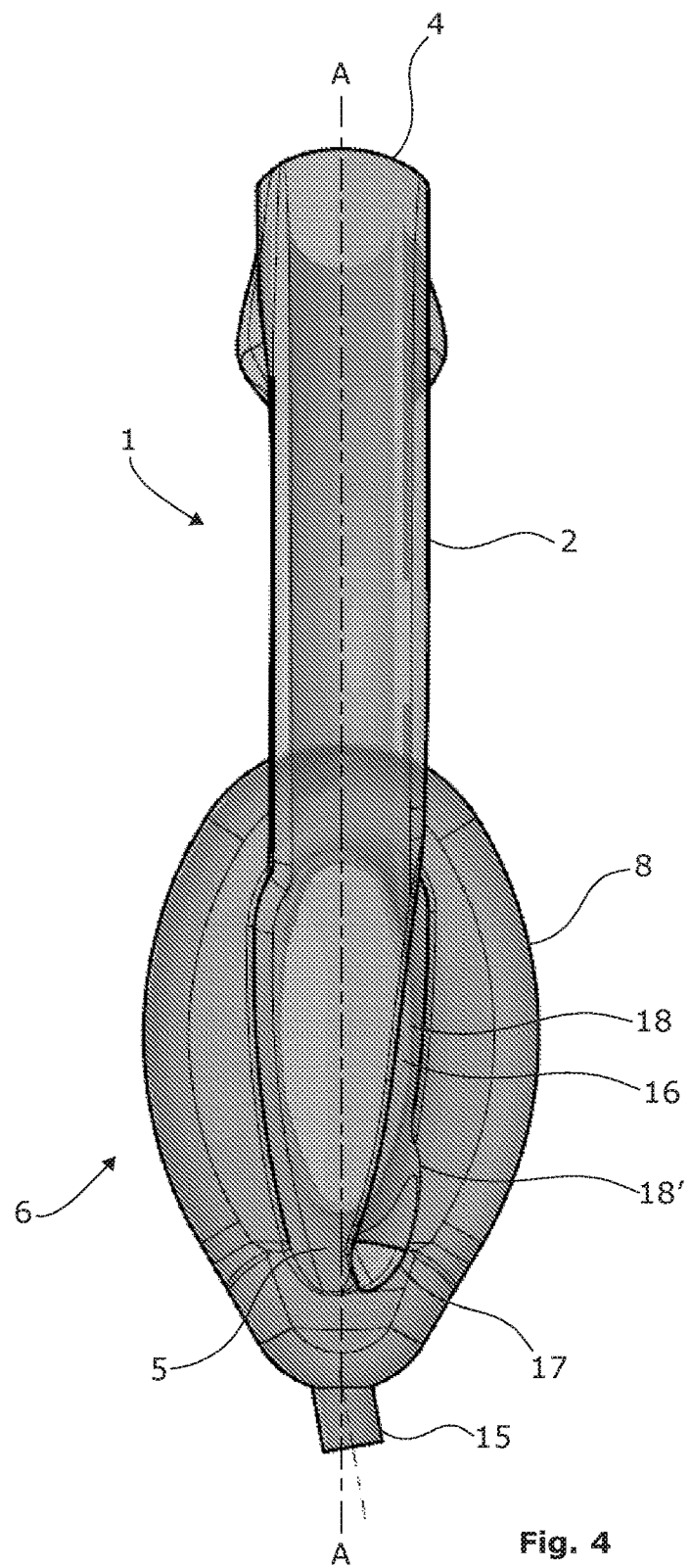
Figure 5:
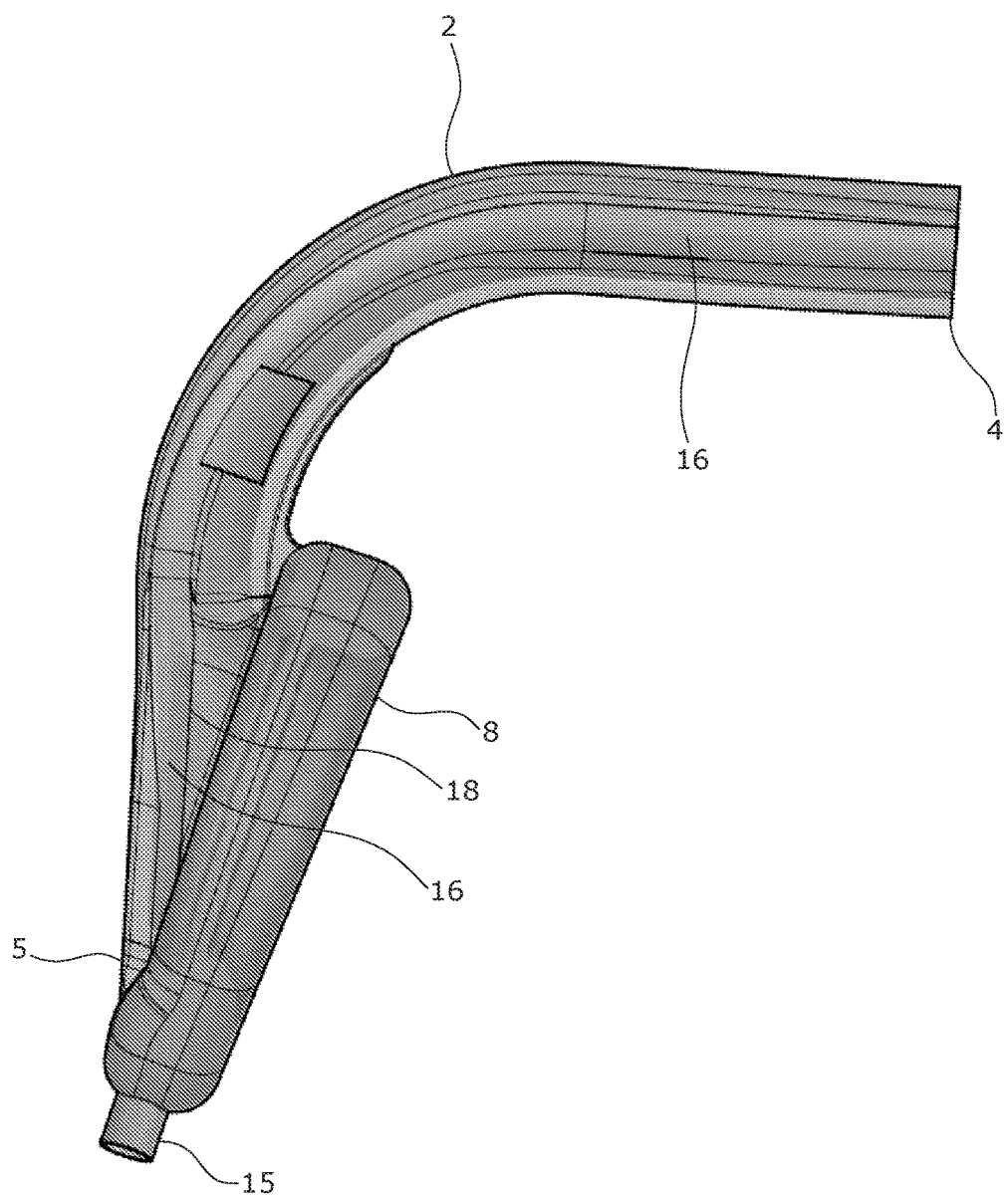

The present invention will now be described in greater detail based on non-limiting exemplary embodiments and with reference to the appended drawings on which FIG. 1 is a perspective view of a laryngeal mask according to the invention, FIG. 2 is a perspective view of the main body of the laryngeal mask of FIG. 1 before assembly with the gastric tube, FIG. 3 is a front view of the main body of the laryngeal mask of FIG. 2, FIG. 4 is a rear view of the main body of the laryngeal mask of FIG. 2, FIG. 5 is a right-hand side view of the main body of the laryngeal mask of FIG. 2, and FIG. 6 is a longitudinal cross section of the laryngeal mask taken along the mirror image symmetry plane indicated by line A-A in FIG. 3.

Turning first to FIG. 1, a perspective view of a laryngeal mask 1 according to the invention is shown. The laryngeal mask comprises an airway tube 2 with a predetermined curvature. As best seen in FIGS. 3 and 6 the airway tube 2 has an inner lumen 3 extending from the proximal end 4 of the airway tube 2 to the distal end 5 of the airway tube 2. At the distal end 5 of the airway tube 2, the airway tube 2, and hence the inner lumen 3, terminates in a somewhat acute angle and possible flares out to form part of a mask portion 6. As can be seen in e.g. FIG. 3, the inner lumen 3 of the airway tube 2 thus communicates with or forms a mask lumen 7 in the mask portion 6. Both the mask lumen 7 at the distal end of the airway tube 2 and the inner lumen 3 at the proximal end 4 of the airway tube 2 are open, the airway tube 2 thus providing a through passage via which air may be supplied to and removed from the lungs during respiration. More specifically, the airway tube and the mask portion are configured to allow intubation of an endotracheal tube while the laryngeal mask is positioned in a patient. At the mask portion 6 a circumferential, inflatable cuff 8 is arranged so as to surround and delimit the mask lumen 7. The airway tube 2 and the mask portion 6 including the inflatable cuff 8 are preferably moulded as a single piece, the inflatable cuff 8 being formed by gluing parts thereof together subsequent to moulding. FIG. 6 shows such a single piece as moulded, i.e. before the parts thereof are glued together. As can be seen, one part of the cuff 8 has a circumferential bead 19. This bead 19 is adapted to be accommodated in and glued to the cuff 8 in a circumferential groove 20 so as to form an inflatable inner volume 13, which will be described below.

The inflatable cuff 8 thus comprises an inflatable inner volume 13 delimited by a closed tubular member with a closed tubular wall so as to define a generally ring shaped or toroidal inflatable inner volume, i.e. a closed tubular loop. As can be seen from e.g. FIG. 3, in the relaxed state, i.e. as moulded and glued, but not inflated, the cuff 8, and hence the inner volume 13, is not toroidal in a strict sense as it is neither circular in cross section of the tubular member nor in the extension along the loop formed by the tubular member. As can be seen from FIG. 6, the cross-section of the inflatable cuff varies along the length of the closed loop. Moreover, as can be seen in FIG. 3, the closed tubular loop is not circular, but generally elliptical or oval, the oval taken in its literal meaning actually being pointed as an egg towards the distal end of the laryngeal mask 1. The pointed distal end of the laryngeal mask 1 thus presents a tip.

The inflatable cuff 8 may be inflated (and deflated) via an inflation tube 9 extending along one side of airway tube 2, in FIG. 1 the invisible left-hand side of the airway tube 2, i.e. as explained above the side towards the left-hand side of the patient when the laryngeal mask 1 is correctly inserted into the patient. The inflation tube thus extends along the outer surface of the airway tube 2. At the distal end (not visible) of the inflation tube 9 the inflation tube 9 is in communication with the inflatable cuff 8. At the proximal end of the inflation tube 9 attachment means 10 are provided. The attachment means 10 allows suitable inflation means (not shown), such as a syringe, for inflating the cuff 8 with a suitable amount of air, to be attached to the inflation tube 9.

On the visible right-hand side of the airway tube 2 in FIG. 1 a gastric tube 12 extends along the outer surface of the airway tube 2, preferably but not necessarily along the entire length thereof. At a first location towards the distal end 5 of the airway tube 2 the gastric tube 12 penetrates the tubular wall of the circumferential cuff 8. It extends through the inflatable volume 13 and ends in a connection arrangement with the tubular wall of the circumferential cuff 8 at a second location, at the tip of the laryngeal mask 1, so as to present an opening 12' at the distal end of the gastric tube 12. The connection engagement is preferably provided as a short tubular stub 15, which in assembly is inverted from the position shown in FIGS. 2-6 and glued to the outside of gastric tube 12 at the distal end of the gastric tube 12. The tip of the laryngeal mask 1 is adapted to engage into the oesophagus of the patient when the laryngeal mask 1 is correctly positioned in a patient. Gastric access is possible by inserting a probe, a catheter or other relevant means from the proximal end 14 of the gastric tube 12, passing it all the way through the gastric tube 12, and out of the opening 12' provided by the gastric tube 12 in the cuff 8.

The gastric tube 12 is accommodated in a recess 16 in order to maintain as much symmetry as possible. Symmetry is to be understood as mirror symmetry with respect to a central plane in about which the inner lumen 3 is generally mirror symmetric. This central plane corresponds to the longitudinal cross section in FIG. 6 taken along the axis A-A in FIG. 3 and FIG. 4. As can be seen the airway tube 2 has an overall curvature in that central plane so as to preferably fit the anatomy of a patient and allowing correct insertion of the laryngeal mask into the patient. The airway tube thus has an inner lumen following a predetermined curve in a central mirror symmetry plane about which the inner lumen is generally mirror symmetrical. The desire for symmetry reflects the fact that the human body generally also exhibits a large degree of mirror symmetry. Though the predetermined curvature is preferably to fit the anatomy, the skilled person will understand that the actual shape of the predetermined curvature is not of importance for the symmetry considerations of the present invention. The predetermined curvature may therefore include a straight line, e.g. if the airway tube 2 of the laryngeal mask 1 is provided with a high degree of flexibility allowing the airway tube 2 to adapt to the anatomy of the patient.

Despite this desire for symmetry it has been found that minor deviations, some of which have already been described above, will provide major advantages for the manufacturing process without compromising the overall function of the laryngeal mask 1. Thus, as described above, according to the invention, said gastric tube 12 extends along the outer surface of the airway tube 2 in an asymmetrical manner, through said closed tubular wall at a first location arranged asymmetrically with respect to said central plane, through said inflatable volume 13, and ends in a connection to the closed tubular wall at a second location at the tip part so as to provide a passage through said circumferential cuff 8.

As can best be seen in FIG. 4, the cuff 8 has been manufactured with an aperture 17 in the mask portion 6. The aperture 17 is preferably provided directly in the moulding process, but evidently it would also be possible to cut it afterwards. The aperture 17 preferably has a crescent shape, i.e. like the blade of a scythe or a sickle. As can be seen, the aperture 17 is off-set with respect to the central plane, in FIG. 4 to the right of the central plane. The off-set is preferably so large that the central plane does not intersect the aperture 17. Having this offset greatly facilitates the assembly where the gastric tube 12 is inserted through the aperture 17 and glued to the short tubular stub 15 which has been inverted into the inner volume 13. Subsequently, the cuff 8 is sealed by gluing the edges of the cuff 8 at the back to the cuff 8 itself around the mask lumen 7, and by gluing the edges of the aperture 17 to the gastric tube 12. As to the stub 15 it should be noted that it is generally co-incident with the tip part of the mask portion 6 of the laryngeal mask 1, but is moulded with a slight angle with respect to the central axis A-A, as can best be seen in FIG. 4. This angle is selected in such a way that when inverted, the short stub 15 points towards the side of the plane in which the aperture 17 is off-set, preferably towards the aperture and recess 16 leading to the aperture 17.

However, since for symmetry reasons the off-set of the aperture 17 should be kept small, the recess 16 cuts quite deeply into the outer surface of the airway tube 2 close to the aperture 17. Accordingly, the wall thickness of the airway tube 2 becomes very small in the area close to the aperture 17, and will not support the gastric tube 12 as well as could be desired. It has, however been found that this can be mitigated by increasing the support of the gastric tube 12 along a length of the airway tube 2 away from the aperture 17 towards the proximal end of the airway tube 2. Preferably this is done by widening the recess 16 adjacent the aperture 17 so as to form a protrusion, such as a salient shelf 18 or ledge, on which the gastric tube 17 may rest and be supported. The gastric tube 17 may be secured to the salient shelf 18 or ledge by gluing. The depth of the recess 16 varies along the length of the airway tube 2. The protrusion preferably only stretches over a relatively short length of the airway tube 2, preferably only in an area on the outer surface of the airway tube 2 corresponding to an area where the inner lumen 3 of the airway tube 2 transitions into the mask lumen 7, i.e. where the airway tube 2 has a taper towards the tip of the mask portion 6 of the laryngeal mask 1. In particular, in the area 18' adjacent the aperture 17, where the outer wall of the airway tube 2 becomes really thin, the salient shelf 18 may be made extra wide for even better support.

As a final remark, it should be noted that the present invention has been described with reference to exemplary embodiments only. The skilled person will know that numerous modifications and variations are possible without deviating from the scope of the invention.

The invention claimed is:

1. A laryngeal mask comprising:
    an airway tube having an inner lumen following a predetermined curve in a central mirror symmetry plane about which the inner lumen is generally mirror symmetrical, an outer surface, a proximal end, and a distal end,
    a mask portion being arranged around the distal end of the airway tube and having a proximal end opposite a distal end thereof, said mask portion comprising a circumferential cuff comprising an inner volume delimited by a closed tubular wall arranged at a periphery of the mask portion and defining, together with the distal end of the airway tube, a mask lumen, the inner lumen of the airway tube thus being in fluid communication with the mask lumen, the circumferential cuff having a shape presenting a tip part at the distal end of the mask portion; and
    a gastric tube which extends along the outer surface of the distal end of the airway tube without penetrating into the mask lumen, penetrates through said closed tubular wall at a first location, extends through said inner volume, and ends in a connection to an opening in the closed tubular wall at a second location, at the tip part, so as to provide a passage through said circumferential cuff, wherein with respect to said central mirror symmetry plane said gastric tube extends along the outer surface of the airway tube in an asymmetrical manner, said first location being arranged asymmetrically with respect to said central mirror symmetry plane.

2. A laryngeal mask according to claim 1, wherein at said distal end of said mask portion the circumferential cuff comprises a back side opposite a front side, wherein said first location is arranged at the back side of the circumferential cuff.

3. A laryngeal mask according to claim 1, wherein said outer surface comprises a recess adapted to accommodate the gastric tube.

4. A laryngeal mask according to claim 3, wherein the recess has a depth that varies along the length of the airway tube.

5. A laryngeal mask according to claim 4, wherein the outer surface of the airway tube presents a protrusion adjacent said recess so as to increase the depth of said recess.

6. A laryngeal mask according to claim 4, further comprising a salient shelf provided adjacent the recess at the distal end of the airway tube to support the gastric tube.

7. A laryngeal mask according to claim 1, wherein the connection comprises a short stub provided at a non-zero angle relative to the central mirror symmetry plane.

8. A laryngeal mask according to claim 7, wherein the central mirror symmetry plane passes through the opening at the second location, and wherein at the distal end of the mask portion the circumferential cuff comprises a back side opposite a front side, and once assembled with the gastric tube the short stub is positioned between the front side and the back side.

9. A laryngeal mask according to claim 8, further comprising a crescent shape opening at the first location, wherein the central mirror symmetry plane does not pass through the opening at the first location.

10. A laryngeal mask according to claim 2, further comprising a crescent shape opening at the first location, the crescent shape opening being configured to receive the gastric tube therethrough.

11. A laryngeal mask according to claim 1, wherein the proximal end of the airway tube and the distal end of the airway tube are molded in one single piece.

12. A laryngeal mask according to claim 11, wherein the airway tube and the circumferential cuff are molded in one single piece.

13. A laryngeal mask according to claim 1, wherein the distal end of the airway tube and the gastric tube, together, present a substantially symmetric profile relative to the central mirror symmetry plane.

14. A laryngeal mask according to claim 13, wherein the distal end of the airway tube comprises a recess to accommodate the gastric tube and a salient shelf adjacent the recess to support the gastric tube, and wherein the distal end of the airway tube is comprised of an airway tube wall having a first thickness adjacent the salient shelf and a second, larger, thickness, the first thickness, the recess, and the salient shelf configured to provide the substantially symmetric profile while sufficiently supporting the gastric tube at the distal end of the mask portion.

15. A laryngeal mask comprising:
an airway tube having an inner lumen following a predetermined curve in a central mirror symmetry plane about which the inner lumen is generally mirror symmetrical, an outer surface, a proximal end, and a distal end, a mask portion being arranged around the distal end of the airway tube and having a proximal end opposite a distal end thereof, said mask portion comprising a circumferential cuff comprising an inner volume delimited by a closed tubular wall arranged at a periphery of the mask portion and defining, together with the distal end of the airway tube, a mask lumen, the inner lumen of the airway tube thus being in fluid communication with the mask lumen, the circumferential cuff having a shape presenting a tip part at the distal end of the mask portion; and a gastric tube which extends along the outer surface of the distal end of the airway tube without penetrating into the mask lumen, penetrates through said closed tubular wall at a first location, extends through said inner volume, and ends in a connection to an opening in the closed tubular wall at a second location, at the tip part, so as to provide a passage through said circumferential cuff, wherein with respect to said central mirror symmetry plane said gastric tube extends along the outer surface of the airway tube in an asymmetrical manner, said first location being arranged asymmetrically with respect to said central mirror symmetry plane, and wherein at said distal end of said mask portion the circumferential cuff comprises a back side opposite a front side, wherein said first location is arranged at the back side of the circumferential cuff, wherein the distal end of said airway tube comprises a recess adapted to accommodate the gastric tube.

16. A laryngeal mask according to claim 15, wherein the distal end of the airway tube comprises a salient shelf adjacent the recess to support the gastric tube, and wherein the distal end of the airway tube is comprised of an airway tube wall having a first thickness adjacent the salient shelf and a second, larger, thickness, the first thickness, the recess, and the salient shelf configured to provide a substantially symmetric profile relative to the central mirror symmetry plane.

17. A method of manufacturing a laryngeal mask, the method comprising:
moulding an airway tube together with a tubular wall, the airway tube having an inner lumen following a predetermined curve in a central mirror symmetry plane about which the inner lumen is generally mirror symmetrical, an outer surface, a proximal end, a distal end, and an intermediate portion between the proximal end and the distal end, the distal end of the airway tube comprising a recess to accommodate a gastric tube and a salient shelf adjacent the recess to support the gastric tube, the tubular wall comprising an edge bonded to the airway tube during said moulding and a free edge;
after moulding the airway tube together with the tubular wall:
bonding the free edge of the tubular wall to form a circumferential cuff having an inner volume delimited by the tubular wall, the circumferential cuff arranged at a periphery of the distal end of the airway tube and forming, together with the distal end of the airway tube, a mask lumen, the inner lumen of the airway tube thus being in fluid communication with the mask lumen, the circumferential cuff having a shape presenting a tip part at a distal end of the laryngeal mask, wherein at said distal end of the laryngeal mask the circumferential cuff comprises a proximal side opposite a distal side;

inserting the gastric tube through an opening in the proximal side;

connecting a distal end of the gastric tube to the distal side;

bonding the gastric tube to seal the opening in the proximal side;

accommodating the gastric tube in the recess; and bonding the gastric tube to the airway tube.

18. A method of manufacturing a laryngeal mask as in claim 17, wherein the free edge of the tubular wall comprises a bead, the method further comprising inserting the bead into a groove to form the circumferential cuff.

19. A method of manufacturing a laryngeal mask as in claim 17, wherein bonding the gastric tube to seal the opening in the back side is performed before bonding the free edge of the tubular wall to form a circumferential cuff.

* * * * *